United States Patent [19]

Immel et al.

[11] 4,097,540

[45] Jun. 27, 1978

[54] PROCESS FOR THE PREPARATION OF 2-ALKYL-2-METHYLPROPANE-1,3-DIOL

[75] Inventors: Otto Immel, Krefeld; Hans-Helmut Schwarz, Krefeld-Traar; Oskar Weissel, Krefeld, all of Germany

[73] Assignee: Bayer Aktiengesellschaft, Leverkusen, Germany

[21] Appl. No.: 822,963

[22] Filed: Aug. 8, 1977

[30] Foreign Application Priority Data

Aug. 27, 1976 Germany ............................ 2638733

[51] Int. Cl.$^2$ ............................................. C07C 29/14
[52] U.S. Cl. ................................. 568/862; 260/601 R; 568/879; 568/881
[58] Field of Search .................................. 260/635 A

[56] References Cited

U.S. PATENT DOCUMENTS

| 2,400,724 | 5/1946 | Walker | 260/635 A |
| 3,808,280 | 4/1974 | Merger et al. | 260/635 A |
| 3,965,193 | 6/1976 | Goetz et al. | 260/601 R |

FOREIGN PATENT DOCUMENTS

| 453,545 | 12/1948 | Canada | 260/635 A |

*Primary Examiner*—Joseph E. Evans
*Attorney, Agent, or Firm*—Burgess, Dinklage & Sprung

[57] ABSTRACT

A process for the preparation of a dihydric alcohol with the formula

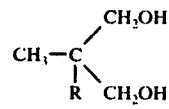

wherein R represents an alkyl radical of 1 to 20 carbon atoms which comprises contacting a 2-alkylacrylaldehyde of the formula

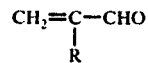

wherein R has the meaning given above with formaldehyde and thereafter contacting the resultant reaction mixture with hydrogen in the presence of a hydrogenation catalyst.

14 Claims, No Drawings

PROCESS FOR THE PREPARATION OF 2-ALKYL-2-METHYLPROPANE-1,3-DIOL

The invention relates to a process for the preparation of 2-alkyl-2-methylpropane-1,3-diols, such as, for example, 2,2-dimethylpropane-1,3-diol or 2-ethyl-2-methylpropane-1,3-diol, by reacting a 2-alkyl-acrylaldehyde with formaldehyde and subsequently hydrogenating the reaction mixture with hydrogen in the presence of catalysts.

Dihydric alcohols of the type mentioned are of industrial importance for the preparation of plasticisers, lacquer raw materials, polyesters and polyurethanes.

2,2-Dimethylpropane-1,3-diol is known as a major industrial product which, in general, is prepared by reducing the hydroxypivaldehyde formed from the aldol condensation of isobutyraldehyde and formaldehyde (compare, for example, Ullmanns Encyclopädie der technischen Chemie (Ullmann's Encyclopaedia of Industrial Chemistry), 4th edition, volume 7 (1974), page 228).

The processes used industrially for the preparation of this compound have considerable disadvantages. When the intermediate compound 2,2-dimethyl-3-hydroxypropanal is prepared by an aldol condensation of isobutyraldehyde and formaldehyde, undesired by-products, such as isobutyraldol and, as a result of the Cannizzaro reaction or the Tischenko reaction, various mixed esters and acid products are formed. The second reaction stage, in which the conversion of 2,2-dimethyl-2-hydroxypropanal in neopentylglycol is effected, also has the disadvantage that, as a result of the reaction known as the Cannizzaro reaction, large amounts of formaldehyde are consumed and an alkali metal formate is formed, the separation of which presents difficulties (compare, for example, DOS German Published Specification No. 2,045,669).

Surprisingly, a process of general applicability for the preparation of dihydric alcohols of the formula

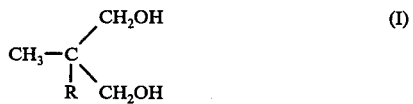

wherein R denotes an alkyl group with 1 to 20 carbon atoms, has now been found which is characterised in that 2-alkylacrylaldehydes of the formula

wherein R has the meaning already indicated, are reacted with formaldehyde and the resulting reaction mixture is treated with hydrogen in the presence of a hydrogenation catalyst. Possible alkyl radicals R are, preferably, those with 1–20 C atoms and preferentially with 1–12 C atoms. Individual examples of alkyl radicals which may be mentioned are methyl, ethyl, propyl, n-butyl, i-butyl, pentyl, hexyl, isoheptyl, dodecyl and pentadecyl.

In the first reaction stage a 2-alkylacrylaldehyde is reacted with formaldehyde in a molar ratio of 0.2:1 to 5:1 and preferably of 0.3:1 to 3:1. Formaldehyde is used in the form of an aqueous solution of formaldehyde and in general in the form of a 30–40% strength by weight solution. The reaction is carried out continuously or discontinuously at 20° to 100° C and preferably at 60°–90° C. The reaction is optionally carried out in the presence of acid substances, for example of an acid, preferably a weak acid, or a solid having acid character, or of an ion exchanger, which can be either a cation exchanger or an anion exchanger.

Acids which can be used are, for example: formic acid, acetic acid, propionic acid, butyric acid, oxalic acid, succinic acid and adipic acid, benzenesulphonic acid and p-toluenesulphonic acid. Sulphuric acid and phosphoric acid, as well as the acid salts of these mineral acids, can also be used. The reaction can also be carried out in the presence of the following solids having acid character: silica gel, kieselguhr, bleaching earth, bentonites and synthetically prepared aluminium silicates.

A preferred embodiment of the first reaction stage is the reaction carried out in the presence of ion exchangers, preferably cation exchangers or anion exchangers.

The reaction according to the invention can accordingly be carried out in the presence of cation exchangers or anion exchangers. Very diverse types of acid or basic exchangers can be used in this case. For example, the synthetic resin ion exchangers obtained from sulphonated styrene/divinyl copolymers, from styrene/acrylic acid copolymers, from vinylbenzyltrimethylammonium polymers and from those which are synthesised from phenolic resins can be employed. (Compare, for example, Ullmanns Encyclopädie der technischen Chemie (Ullmann's Encyclopaedia of Industrial Chemistry), 3rd edition, volume 8 (1957), page 812-817).

Examples of suitable ion exchangers are those listed in Houben-Weyl, Methoden der Org. Chem. (Methods of Organic Chemistry), volume I/1, page 528–529, Stuttgart 1958.

The anion exchangers used are preferably those which contain tetraalkylammonium groups. These are preferably employed in the chloride form.

Cation exchangers which can be used are preferred ion exchangers which contain sulphonic acid groups, for example those which are based on polystyrene and are crosslinked with divinylbenzene.

These cation exchangers can also be employed in the Na form.

In order to improve the thorough mixing and thus to accelerate the reaction, solubilising agents, such as, for example, methanol, ethanol, isopropanol, dioxane or tetrahydrofurane, can be added. The amount of solvent required depends on the nature of the solvent; thus, for example 0.5–2 mols of dioxane are required per mol of 2-ethylacrylaldehyde.

If the process is carried out discontinuously, for example in a stirred vessel, the reaction can be carried out as follows:

The 2-alkylacrylaldehyde and formaldehyde are combined in a molar ratio of 1:1 to 1:3. The solubilising agent is then added. The amount of ion exchanger used is determined by the 2-alkylacrylaldehyde employed: 0.3 to 2 parts by weight of ion exchanger are used per 1 part by weight of 2-alkylacrylaldehyde. The reaction mixture is kept at a temperature of about 60°–90° C for 10 minutes to 6 hours, whilst stirring. 0.005 part by weight of hydroquinone, for example, can be added as a stabiliser for the 2-alkylacrylaldehyde compounds employed.

After the ion exchanger has been separated off, the reaction product can be returned to the catalytic hydrogenation without further pretreatment. However, it can also be appropriate to separate off the unconverted 2-alkylacrylaldehyde by distillation or extraction so that this can be re-employed. In general, the hydrogenation is carried out at elevated temperature at about 50° to 170° C, and preferably at 80° to 130° C, and under an elevated pressure of hydrogen, for example under pressures of 50 to 400 bars, and preferably of 100–300 bars.

Suitable catalysts are hydrogenation catalysts which contain, as the active constituent, an element of group VIII of the periodic table and/or of group I *b* of the periodic table, as published in the end papers of Cotton and Wilkinsen "Advance Inorganic Chemistry" Second Edition, for example platinum, ruthenium, cobalt, nickel or copper.

The catalysts can be used in the form of skeletal catalysts, supported catalysts or mixed catalysts.

Particularly suitable catalysts are mixed catalysts based on nickel and cobalt, especially those which contain chromium, aluminium, magnesium, barium, zinc, manganese, thorium and/or copper as further constituents, for example nickel chromite catalysts of the composition Ni-Cr-Al-Cu, Ni-Cr-Zn-Ba or Ni-Cr-Mg-Th-Ba-Cu, or cobalt catalysts of the composition Co-Mg-Cu or Co-Mn-Cu.

The hydrogenation can be carried out either discontinuously or continuously in the customary manner, for example in a stirred autoclave or a reaction tube. Conventional arrangements of apparatus of very diverse types are suitable for carrying out the process according to the invention. It is possible to carry out the hydrogenation as a sump phase process or as a trickle phase process.

As a discontinuous process, the hydrogenation is carried out in the customary manner as a sump phase process in an autoclave in the presence of a pulverulent catalyst.

Particularly advantageously, the hydrogenation can be carried out continuously. This is effected in the customary manner, either using a pulverulent catalyst, for example in accordance with the principle of a bubble column, by passing the liquid starting material, in which the catalyst is suspended, together with hydrogen in co-current through a reactor cascade, or using a particulate catalyst, for example in accordance with the principle of a trickle phase by trickling the starting material in the liquid form over the stationary catalyst located in a reaction tube, whilst the hydrogen is passed through the reaction tube in co-current or counter-current. Advantageously, excess hydrogen is cycled.

For working up, the hydrogenation catalyst is first separated off from the reaction product and this is generally effected by filtering off. The diol can be separated off by distillation under reduced pressure. It is appropriate to carry out the distillation in at least two stages. In the first stage the low-boiling compounds, such as methanol and pentanol and also the organic solvent added in the first reaction stage, are distilled off under normal pressure. The sump product is distilled under 0.1 to 100 mm Hg in a further column in order to separate off and purify the diol.

Unless otherwise stated, the percentage data given in the examples which follow are in mol percent.

EXAMPLE 1

126 g of α-ethylacrolein, 300 g of a 30% strength aqueous solution of formaldehyde, 350 g of 1,4-dioxane, 0.75 g of hydroquinone and 100 g of strongly basic anion exchanger (polyvinyl-benzyl-trimethylammonium chloride) were warmed to 84° C, whilst stirring. After a reaction time of 30 minutes, 184 g of the reaction liquid were separated off and then hydrogenated in an autoclave at 120° C and under 230 to 280 bars of hydrogen. 14.7 g (8%) of a Ni-Cr-Al hydrogenation catalyst were employed for the hydrogenation.

The hydrogenated product was analysed by gas chromatography and the result was converted to obtain the figures for the total batch. This gave 68.7% of 2-ethyl-2-methyl-propane-1,3-diol and 30.7% of 2-methyl-butanol. Since 2-methyl-butanol is the hydrogenation product of ethylacrolein which has not been converted on the ion exchanger, calculation gives a yield of 99% of 2-ethyl-2-methyl-propane-1,3-diol relative to converted α-ethylacrolein.

EXAMPLE 2

84 g of α-ethylacrolein, 400 g of a 30% strength aqueous solution of formaldehyde, 0.75 g of hydroquinone and 400 g of 1,4-dioxane, together with 100 g of macroporous strongly acid cation exchanger (polystyrenesulphonic acid; unactivated Na salt form), were warmed to the boiling point.

After a reaction time of 2 hours, 126 g of the reaction liquid were separated off and hydrogenated as in Example 1. This gave 61.5% of 2-ethyl-2-methyl-propane-1,3-diol and 36% of 2-methyl-butanol, relative to the ethylacrolein employed.

EXAMPLE 3

280 g (4 mols) of α-methylacrolein, 800 g of a 30% strength aqueous solution of formalin, 1 g of hydroquinone, 400 g of 1,4-dioxane and 200 g of strongly basic anion exchanger (poly-vinyl-benzyl-trimethylammonium chloride) were kept at the boiling point for 3 hours, whilst stirring. The reaction solution was separated off from the ion exchanger and hydrogenated as in Example 1. By means of analyses by gas chromatography it was found that the hydrogenated product contained 3.01 mols of 2,2-dimethyl-propane-1,3-diol and 0.84 mol of isobutanol. If isobutanol is regarded as the hydrogenation product of unconverted α-methylacrolein, calculation gives a yield of 95% of 2,2-dimethylpropane-1,3-diol relative to converted α-methylacrolein.

EXAMPLE 4

42 g of ethylacrolein, 100 g of a 30% strength aqueous solution of formalin, 120 g of dioxane and 0.5 g of hydroquinone were combined to give a solution and 33 g of strongly acid cation exchanger (polystyrenesulphonic acid; H$^+$ form) were added.

This mixture was kept at the boiling point (84° C) for 1 hour, whilst stirring. The reaction solution was then separated off from the ion exchanger and hydrogenated in the presence of 8% by weight of a hydrogenation catalyst (Ni-Cr-Al) at 110° C, as in Example 1. 0.28 mol of 2-ethyl-2-2-methylpropane-1,3-diol and 0.18 mol of 2-methylbutanol were found in the hydrogenated product. Calculation gives the yield of 2-ethyl-2-methylpropane-1,3-diol as 87.5%, relative to converted α-ethylacrolein.

EXAMPLE 5

If the reaction is carried out in the same way as in Example 4 but using 33 g of macroporous strongly acid cation exchanger (polystyrenesulphonic acid; H$^+$ form), 55.5% of 2-ethyl-2-methylpropane-1,3-diol and 36% of 2-methylbutanol are obtained, relative to the α-ethylacrolein employed.

EXAMPLE 6

70 g of α-methylacrolein, 200 g of a 30% strength aqueous solution of formaldehyde, 0.5 g of hydroquinone and 100 g of dioxane, together with 50 g of macroporous strongly acid cation exchanger (polystyrenesulphonic acid; H+ form), were kept at the boiling point (72°–74° C) for one hour, whilst stirring.

The reaction liquid separated off from the ion exchanger was hydrogenated in the presence of 8% by weight of hydrogenation catalyst (Ni-Cr-Al), as in Example 1. Analysis of the hydrogenated product showed that 64.6% of the α-methylacrolein employed had been converted to 2,2-dimethyl-propane-1,3-diol, whilst 22% were in the form of isobutanol after the hydrogenation.

EXAMPLE 7

A mixture of 378 g of α-pentylacrolein, 180 g of a 30% strength aqueous solution of formaldehyde, 100 g of 1,4-dioxane and 120 g of strongly basic anion exchanger (poly-vinyl-benzyltrimethylammonium chloride) was kept at 70°–80° C for 3 hours, whilst stirring. The reaction liquid was then separated off from the ion exchanger and hydrogenated as in Example 1. The catalyst particles were filtered off from the hydrogenation mixture. The reaction solution was concentrated under a waterpump vacuum and at 40° C. The evaporation residue was subjected to fractional distillation under a high vacuum. 93 g of 2-methyl-2-pentyl-propane-1,3-diol distilled over under 0.5 mm Hg and at 106°–110° C. The chemical structure of this compound was clarified by recording the NMR spectrum.

EXAMPLE 8

126 g of α-ethylacrolein, 300 g of a 30% strength aqueous solution of formaldehyde, 1 g of hydroquinone and 350 g of 1,4-dioxane were combined at 25° C to give a solution. After about 2 hours, 120 g of this solution, which had a pH value of 2-3, were hydrogenated as in Example 1. Analysis of the hydrogenated product gave 55.9% of 2-ethyl-2-methylpropane-1,3-diol and 34% of methylbutanol, relative to the α-ethylacrolein employed.

The pH value of a further 120 g of the abovementioned solution having a pH value of 2-3 was adjusted to precisely 7.0 with aqueous sodium hydroxide solution prior to the hydrogenation reaction and the hydrogenation was then carried out as in Example 1.

Analysis of the hydrogenated product gave 60.8% of 2-ethyl-2-methyl-propane-1,3-diol and 37.5% of methylbutanol, relative to the ethylacrolein employed.

EXAMPLE 9

A solution of 50 g of ethylacrolein and 0.2 g of hydroquinone in 100 g of dioxane and 40 g of ethanol was adjusted to a pH value of precisely 7.0 with 1 normal sodium hydroxide solution and then combined with 120 g of an accurately neutralised 30% strength aqueous solution of formaldehyde to give a solution in which the pH value adjusted to 4.5–5.0. After the solution had been neutralised it was left to stand for 15 hours at room temperature and was then hydrogenated as in Example 1.

Analysis of the hydrogenated product gave 55.7% of 2-ethyl-2-methyl-propane-1,3-diol and 40.4% of 2-methylbutanol, relative to the ethylacrolein employed.

EXAMPLE 10

50 g of ethylacrolein, 0.2 g of hydroquinone, 100 g of dioxane, 40 g of ethanol and 120 g of a 30% strength aqueous solution of formaldehyde were combined to give a neutral solution, as described in Example 9, and then immediately hydrogenated as in Example 1.

Analysis of the hydrogenated product gave 57.5% of 2-ethyl-2-methyl-propane-1,3-diol and 41.3% of methylbutanol, relative to the ethylacrolein employed.

What is claimed is:

1. A process for the preparation of a dihydric alcohol with the formula

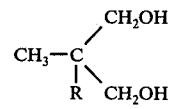

wherein R represents an alkyl radical of 1 to 20 carbon atoms which comprises contacting a 2-alkylacrylaldehyde of the formula

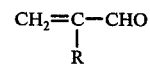

wherein R has the meaning given above with formaldehyde and thereafter contacting the resultant reaction mixture with hydrogen in the presence of a hydrogenation catalyst.

2. A process according to claim 1 wherein the 2-alkylacrylaldehyde is reacted with formaldehyde in a molar ratio of 0.2:1 to 5:1.

3. A process according to claim 1 wherein the reaction is carried out employing a 30 to 40 percent strength by weight aqueous solution of formaldehyde.

4. A process according to claim 1 wherein the reaction is carried out at a temperature of 20 to 100° C.

5. A process according to claim 1 wherein the reaction is carried out in the presence of an acid substance.

6. A process according to claim 1 wherein the reaction is carried out in the presence of an acid or a solid having an acid character or an ion exchanger.

7. A process according to claim 1 wherein the reaction is carried out in the presence of a cation exchanger or an anion exchanger.

8. A process according to claim 1 wherein the reaction is carried out in the presence of a solvent.

9. A process according to claim 8 wherein the solvent is methanol, ethanol, isopropanol, dioxane or tetrahydrofuran.

10. A process according to claim 1 wherein the 2-alkylacrylaldehyde is 2-methylacrylaldehyde.

11. A process according to claim 1 wherein the 2-alkylakrylaldehyde is 2-ethylacrylaldehyde.

12. A process according to claim 1 wherein the hydrogenation is carried out in the presence of a catalyst containing an element of group VIII of the periodic table or an element of sub-group I of the periodic table.

13. A process according to claim 1 wherein the hydrogenation is carried out in the presence of a nickel chromite catalyst.

14. A process according to claim 1 wherein the hydrogenation is carried out at a temperature of 50° to 170° C under a pressure of 50 to 400 bars.

* * * * *